US012611160B2

(12) United States Patent (10) Patent No.: US 12,611,160 B2
Sato (45) Date of Patent: Apr. 28, 2026

(54) ULTRASONIC DIAGNOSTIC DEVICE AND IMAGE PROCESSING DEVICE

(71) Applicant: CANON MEDICAL SYSTEMS CORPORATION, Otawara (JP)

(72) Inventor: Takeshi Sato, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 628 days.

(21) Appl. No.: 17/390,262

(22) Filed: Jul. 30, 2021

(65) Prior Publication Data

US 2022/0054104 A1 Feb. 24, 2022

(30) Foreign Application Priority Data

Jul. 30, 2020 (JP) ................................. 2020-129389

(51) Int. Cl.
  *A61B 8/06* (2006.01)
  *A61B 8/14* (2006.01)
  *G06T 7/262* (2017.01)
(52) U.S. Cl.
  CPC ................. *A61B 8/06* (2013.01); *A61B 8/14* (2013.01); *G06T 7/262* (2017.01); *G06T 2207/10132* (2013.01); *G06T 2207/20004* (2013.01); *G06T 2207/20056* (2013.01); *G06T 2207/30104* (2013.01)
(58) Field of Classification Search
  CPC . A61B 8/06; G06T 7/262; G06T 2207/20004; G06T 2207/20056
  See application file for complete search history.

(56) References Cited

U.S. PATENT DOCUMENTS 5,278,757 A * 1/1994 Hoctor ................ G01S 15/8918
                                                              600/463
5,497,777 A * 3/1996 Abdel-Malek ...... G01S 7/52077
                                                              600/443
(Continued)

FOREIGN PATENT DOCUMENTS

JP      2006-142006 A    6/2006
JP      2011-125635 A    6/2011
(Continued)

OTHER PUBLICATIONS

Japanese Office Action issued Dec. 18, 2024 in Japanese Patent Application No. 2021-125512, 3 pages.

*Primary Examiner* — Kathleen M Broughton
*Assistant Examiner* — Alexander John Rodgers
(74) *Attorney, Agent, or Firm* — Oblon, McClelland, Maier & Neustadt, L.L.P.

(57) ABSTRACT

An ultrasonic diagnostic device according to an embodiment includes a collecting unit and processing circuitry. The collecting unit performs ultrasonic scanning with respect to a subject and collects reflected-wave data. The processing circuitry performs short-time Fourier transform in the depth direction with respect to the reflected-wave data; applies a nonlinear adaptive MTI filter on a frequency-by-frequency basis with respect to the result of the short-time Fourier transform; and performs inverse short-time Fourier transform in the depth direction with respect to the output of the nonlinear adaptive MTI filter. Then, the processing circuitry estimates blood flow information from the result of the inverse short-time Fourier transform.

7 Claims, 14 Drawing Sheets

(56)                    References Cited

U.S. PATENT DOCUMENTS

| | | | | |
|---|---|---|---|---|
| 5,553,618 | A | * | 9/1996 | Suzuki .................. A61B 5/055 |
| | | | | 601/3 |
| 8,858,446 | B2 | | 10/2014 | Sato |
| 2007/0282203 | A1 | | 12/2007 | Baba et al. |
| 2011/0152689 | A1 | * | 6/2011 | Sato ........................ A61B 8/06 |
| | | | | 600/454 |
| 2015/0320395 | A1 | * | 11/2015 | Sato .................... A61B 8/5207 |
| | | | | 600/455 |
| 2017/0086793 | A1 | * | 3/2017 | Sato .................... A61B 8/5207 |
| 2017/0086796 | A1 | * | 3/2017 | Watanabe ........... G01S 7/52026 |
| 2018/0172816 | A1 | * | 6/2018 | Chiu ....................... G01S 13/26 |
| 2019/0369220 | A1 | | 12/2019 | Vignon et al. |
| 2020/0107818 | A1 | * | 4/2020 | Keshet ................ A61B 8/0883 |

FOREIGN PATENT DOCUMENTS

| | | | |
|---|---|---|---|
| JP | 5398514 | B2 | 1/2014 |
| JP | 2014-158698 | A | 9/2014 |
| JP | 2016-2379 | A | 1/2016 |
| JP | 2019-054938 | A | 4/2019 |
| JP | 2019-535448 | A | 12/2019 |

* cited by examiner

RANGE DIRECTION
RF SIGNALS

μs

DOPPLER DIRECTION
IQ SIGNALS ms

DOPPLER
FREQUENCY

Hz

RANGE DIRECTION
RF SIGNALS

DOPPLER DIRECTION
IQ SIGNALS

DOPPLER
FREQUENCY

RANGE DIRECTION
RF SIGNALS

DOPPLER DIRECTION
IQ SIGNALS

DOPPLER
FREQUENCY

RANGE DIRECTION
RF SIGNALS

DOPPLER DIRECTION
IQ SIGNALS

DOPPLER
FREQUENCY (1) PRIMARY SIGNALS

ULTRASONIC DIAGNOSTIC DEVICE AND IMAGE PROCESSING DEVICE

CROSS-REFERENCE TO RELATED APPLICATIONS

This application is based upon and claims the benefit of priority from Japanese Patent Application No. 2020-129389, filed on Jul. 30, 2020; the entire contents of which are incorporated herein by reference.

FIELD

Embodiments described herein relate generally to an ultrasonic diagnostic device and an image processing device.

BACKGROUND

In recent years, Power Doppler imaging is performed that has high resolution in the broadband of single-wave transmission or two-wave transmission. However, if the transmission pulses have a large bandwidth; then the doppler frequency signals spread out, thereby resulting in overlapping of the Doppler signals of the blood flow and the Doppler signals of the tissue movement. For that reason, in a moving target indication (MTI) filter it becomes a difficult task to separate the blood flow and the tissues. Particularly, if a point reflector obliquely cuts across the ultrasonic beams, there occurs a phenomenon called "transit-time intrinsic spectral broadening" in which the Doppler frequency spreads out because the Doppler signals at the same observation point undergo amplitude modulation that is dependent on the azimuth resolution. This phenomenon occurs more conspicuously in proportion to a high depth (range) resolution and a high azimuth resolution. In the case of specular reflection signals, since the changes occur at minute angles, the azimuth resolution becomes equal to or greater than the acoustic field. That escalates the problem. Moreover, if the signals get saturated in an analog-to-digital converter (ADC), there is a further increase in the spread of the Doppler frequency.

FIG. 1 is a diagram illustrating an example in which a point reflector obliquely cuts across the ultrasonic beams. In FIG. 1, the following is illustrated: an acoustic field 90 of a point object (a point reflector) that moves obliquely with respect to the ultrasonic beams; and a fixed observation point 91. For example, with reference to FIG. 1, the point object moves in the direction of 45° with respect to the direction of travel of the ultrasonic beams. Thus, with reference to FIG. 1, an angle of 45° is formed between the direction of movement of the point object and the direction of travel of the ultrasonic beams.

FIGS. 2A to 2L are diagrams illustrating examples of various types of signals that are measured at the observation point 91 illustrated in FIG. 1. In FIGS. 2A to 2F are illustrated examples of various types of signals measured in the case in which an angle of 0° is formed between the direction of movement of the point object and the direction of travel of the ultrasonic beams. In FIGS. 2G to 2L are illustrated examples of various types of signals measured in the case in which an angle of 45° is formed between the direction of movement of the point object and the direction of travel of the ultrasonic beams. Moreover, in the case illustrated in FIGS. 2A to 2C and FIGS. 2G to 2I, there is no signal saturation in the ADC. On the other hand, in the case illustrated in FIGS. 2D to 2F and FIGS. 2J to 2L, there is signal saturation in the ADC.

In FIGS. 2A, 2D, 2G, and 2J are illustrated examples of RF signals in the range direction. More particularly, in each of FIGS. 2A, 2D, 2G, and 2J is illustrated four instances, from the first instance to the fourth instance, of reception of signals (RF signals) in response to one of four instances of transmission of ultrasonic waves. In FIGS. 2A, 2D, 2G, and 2J; the horizontal axis represents the time, that is, the range direction; and the vertical axis represents the transmission order. For example, reception signals received in response to the first instance of transmission, reception signals received in response to the second instance of transmission, reception signals received in response to the third instance of transmission, and reception signals received in response to the fourth instance of transmission are respectively illustrated in FIGS. 2A, 2D, 2G, and 2J.

In each of FIGS. 2B, 2E, 2H, and 2K is illustrated an example of four IQ signals in the Doppler direction that are generated from four IQ signals in the range direction generated from the four RF signals illustrated in FIGS. 2A, 2D, 2G, and 2J, respectively. In FIGS. 2B, 2E, 2H, and 2K; the horizontal axis represents the time, that is, the Doppler direction; and the vertical axis represents the amplitude.

In FIGS. 2C, 2F, 2I, and 2L are illustrated examples of the Doppler shift calculated using the IQ signals illustrated in FIGS. 2B, 2E, 2H, and 2K, respectively. In FIGS. 2C, 2F, 2I, and 2L; the horizontal axis represents the Doppler frequency, and the vertical axis represents the decibels.

If FIGS. 2C and 2I are compared, it can be understood that the spread of the Doppler frequency has increased because the point object obliquely cuts across the ultrasonic beams. Moreover, if FIGS. 2I and 2L are compared, it can be understood that the spread of the Doppler frequency has further increased because of signal saturation in the ADC.

In this way, when the Doppler frequency widely spreads, there is overlapping of the Doppler frequency of blood flow signals and the Doppler frequency of the signals of the movement of the tissues overlap each other, and the two types of Doppler frequency become inseparable in a normal MTI filter. Moreover, when there is movement of a small intensive reflector or when specular reflection occurs, the minor intensive reflection or the specular reflection is difficult to remove even using an MTI filter in which principal component analysis is used, because the small intensive reflector or the specular reflector does not represent a principal component. Regarding such an MTI filter in which principal component analysis is used, for example, the disclosure is given in Patent Literature (Japanese Patent Application Laid-open No. 2014-158698).

On the other hand, in the case of long pulse transmission such as about 16-wave transmission, there is no spreading of the Doppler frequency and there is an increase in the duration of the small intensive reflector signals or the specular reflection signals, thereby making it easier to remove those signals using an MTI filter. However, the range resolution undergoes a decline.

If Fourier transform is performed with respect to the range direction, then it is possible to think of the individual frequencies in the same manner as in the case of continuous waves. Based on that way of thinking, a method (a separation method) is known in which the RF frequencies and the Doppler frequencies are treated as two-dimensional signals and are respectively subjected to different types of quadrature transform, and the clutter component and the blood flow component are separated. Regarding such a separation method, the disclosure is given in Patent Literature (Japanese Patent Application Laid-open No. 2011-125635).

DETAILED DESCRIPTION

Figure 1:
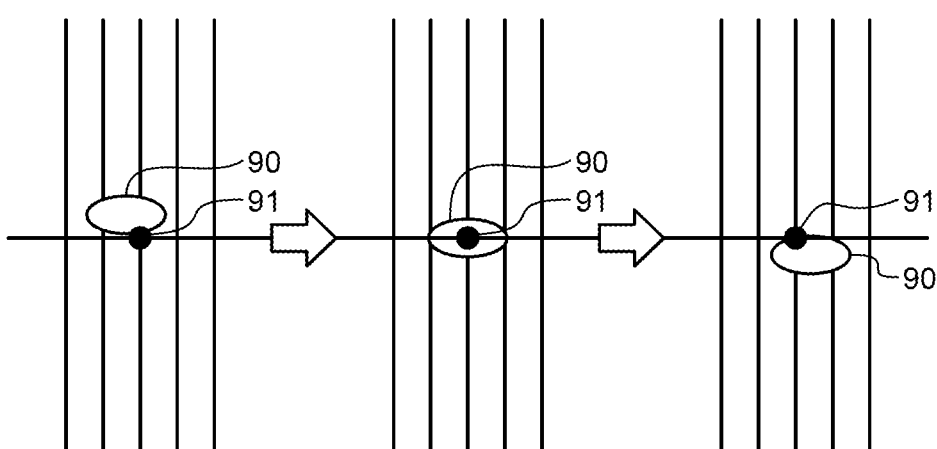
FIG. 1 is a diagram illustrating an example in which a point reflector obliquely cuts across ultrasonic beams.
Figure 2A:
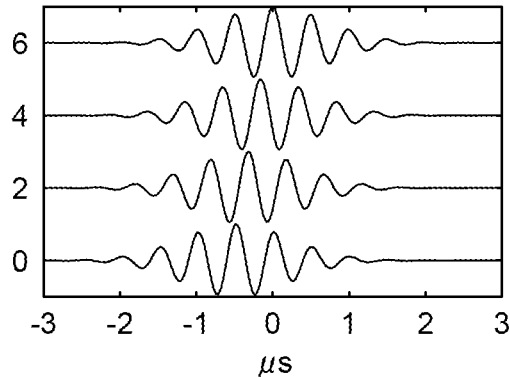
FIGS. 2A to 2L are diagrams illustrating examples of signals that are measured at an observation point illustrated in FIG. 1.
Figure 2B:
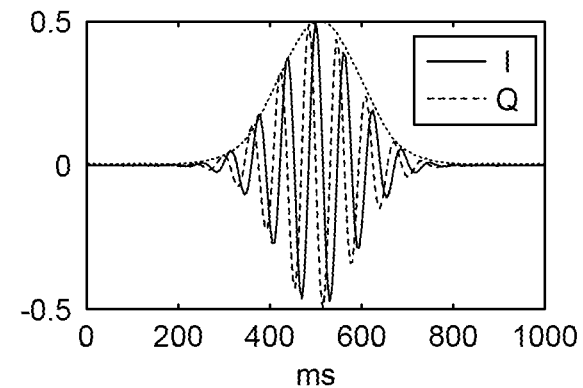
Figure 2C:
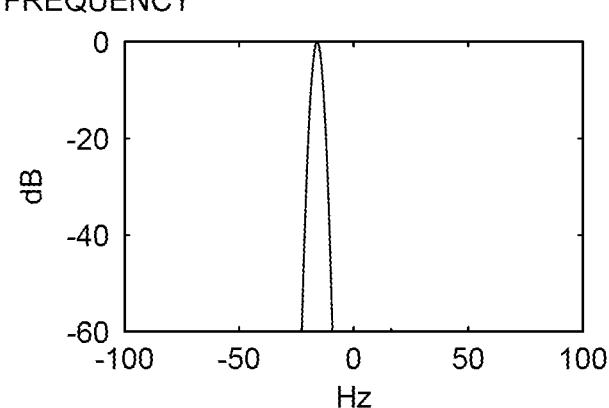
Figure 2D:
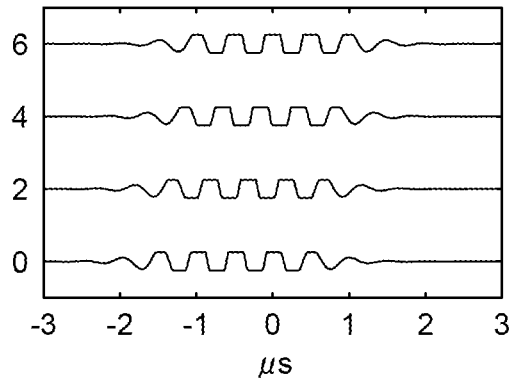
Figure 2E:
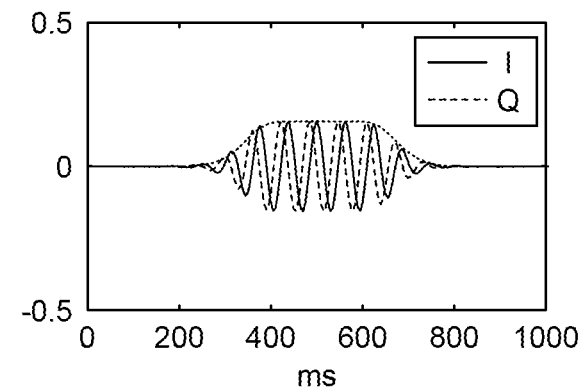
Figure 2F:
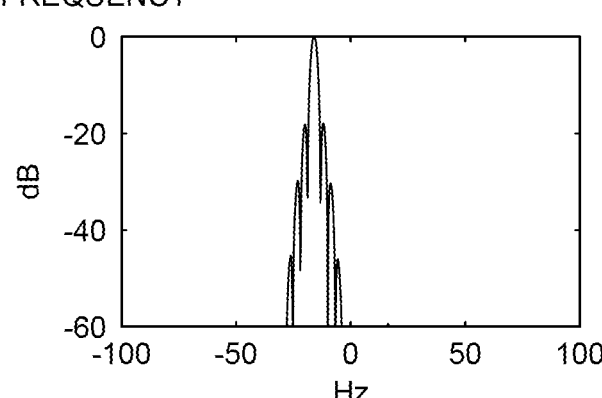
Figure 2G:
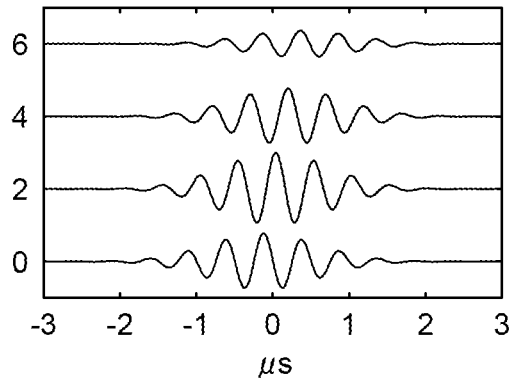
Figure 2H:
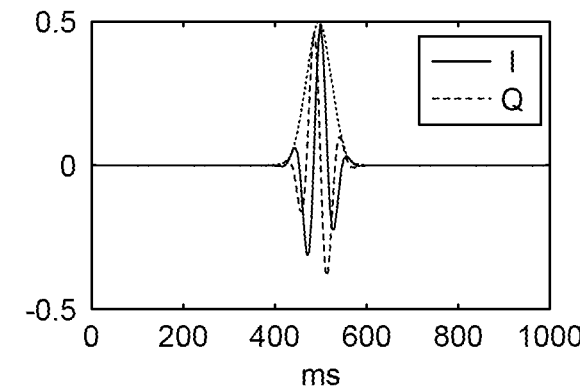
Figure 2I:
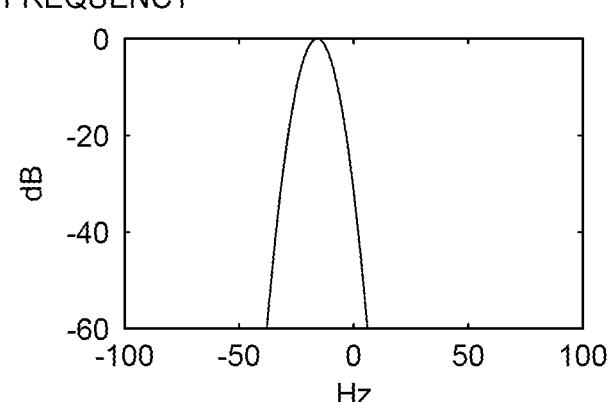
Figure 2J:
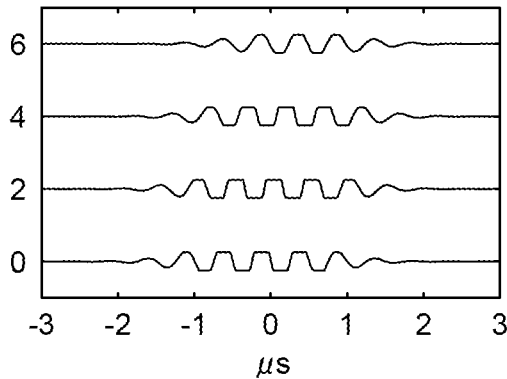
Figure 2K:
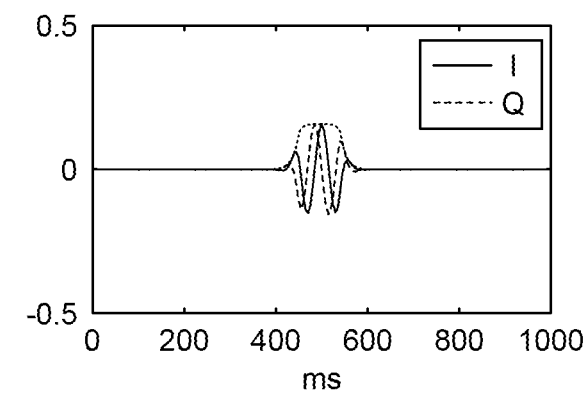
Figure 2L:
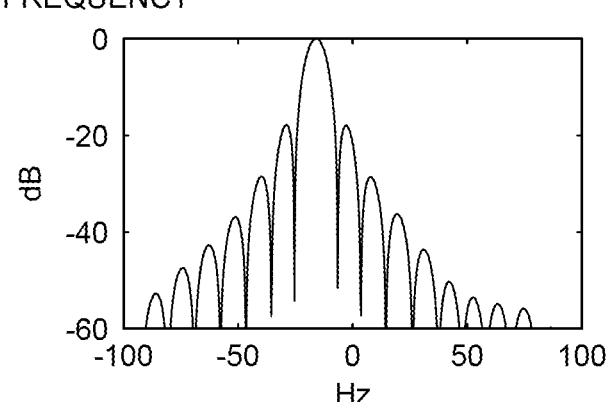

An ultrasonic diagnostic device according to embodiments includes a collecting unit and processing circuitry. The collecting unit performs ultrasonic scanning with respect to the subject and collects reflected-wave data. The processing circuitry performs short-time Fourier transform in the depth direction with respect to the reflected-wave data; applies a nonlinear adaptive MTI filter on a frequency-by-frequency basis with respect to the result of short-time Fourier transform, and performs inverse short-time Fourier transform in the depth direction with respect to the output of the nonlinear adaptive MTI filter. Then, from the result of the inverse short-time Fourier transform, the processing circuitry estimates blood flow information.

Exemplary embodiments and modification examples of the ultrasonic diagnostic device and an image processing device are described below in detail with reference to the accompanying drawings. However, the ultrasonic diagnostic device and the image processing device according to the application concerned are not limited by the embodiments described below. Moreover, the embodiments can be combined with other embodiments, other modification examples, and the conventional technology without causing any contradictions in the contents. Furthermore, in the following explanation, identical constituent elements are referred to by the same reference numerals, and their explanation is not repeated.

First Embodiment

Figure 3:
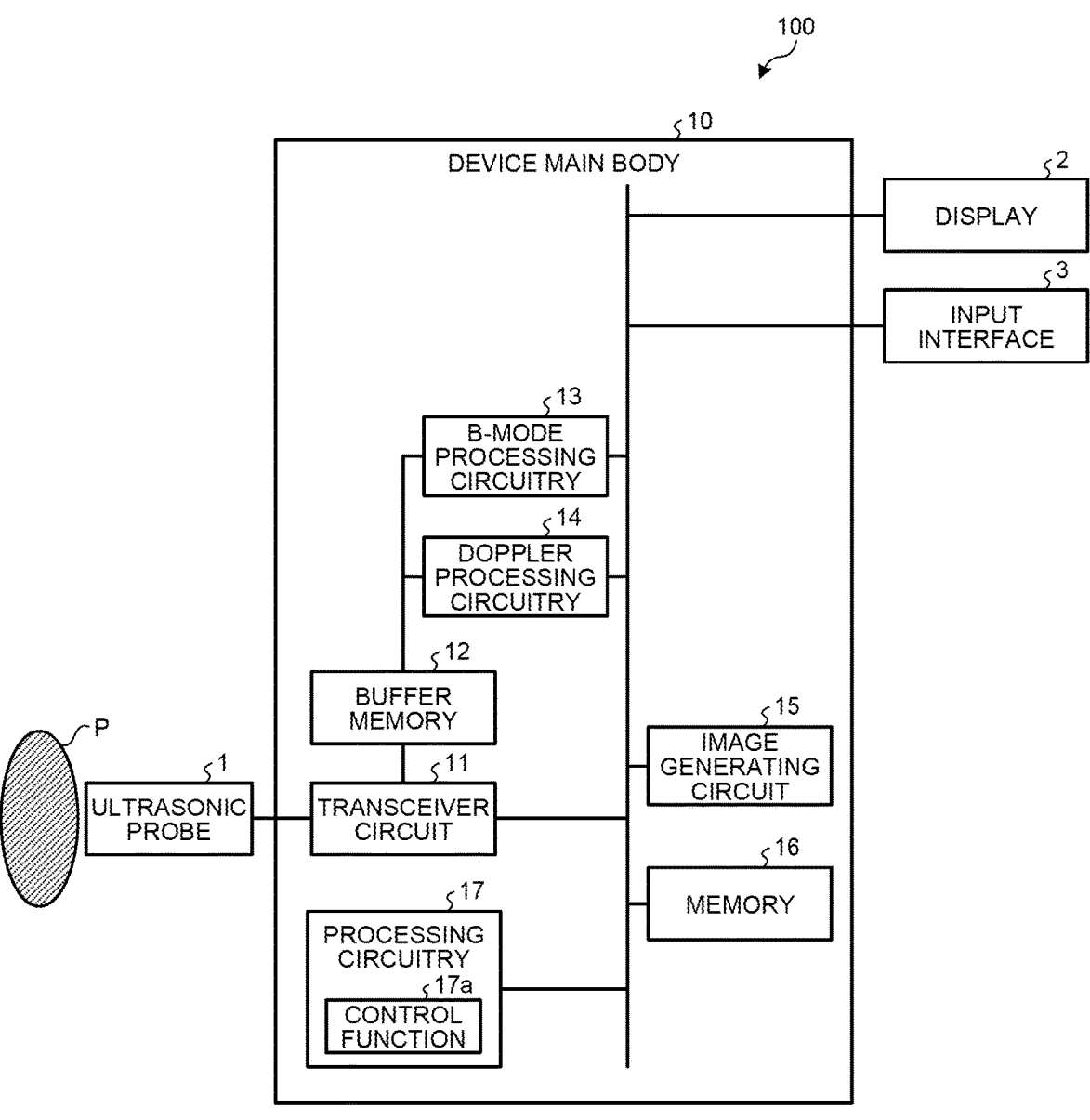
FIG. 3 is a diagram for explaining an exemplary configuration of an ultrasonic diagnostic device according to a first embodiment.

Firstly, the explanation is given about an exemplary configuration of an ultrasonic diagnostic device according to a first embodiment. FIG. 3 is a diagram for explaining an exemplary configuration of an ultrasonic diagnostic device 100 according to the first embodiment. As illustrated in FIG. 3, the ultrasonic diagnostic device 100 according to the first embodiment includes an ultrasonic probe 1, a display 2, an input interface 3, and a device main body 10.

The ultrasonic probe 1 performs ultrasonic scanning with respect to a subject P. The ultrasonic probe 1 is connected to the device main body 10 in a detachably-attachable manner. When ultrasonic waves are transmitted from the ultrasonic probe 1 to the subject P, the transmitted ultrasonic waves get reflected one after another from the discontinuous surfaces of the acoustic impedances in the body tissues. Then, the ultrasonic probe 1 receives the reflected ultrasonic waves as reflected waves (echo). Subsequently, the ultrasonic probe 1 converts the reflected waves into reflected-wave signals. The amplitude of the reflected-wave signals is dependent on the differences in the acoustic impedances in the discontinuous surfaces from which the ultrasonic waves get reflected. Meanwhile, the reflected-wave signals that are obtained when the transmitted ultrasonic pulses that are reflected from the moving blood flow or from the cardiac wall become dependent on the velocity component with respect to the ultrasonic wave transmission direction of the moving body due to the Doppler effect, and undergo a frequency shift. Then, the ultrasonic probe 1 outputs the reflected-wave signals to the device main body 10. The ultrasonic probe 1 can be a convex probe or a sectored probe. Thus, various types of ultrasonic probes can be used as the ultrasonic probe 1.

In the case of performing scanning of a two-dimensional region (i.e., performing two-dimensional scanning) inside the subject P using the ultrasonic probe 1; for example, the user connects a 1D array probe, which has a plurality of transducers (piezoelectric transducers) arranged therein, as the ultrasonic probe 1 to the device main body 10. The 1D array probe is a linear ultrasonic probe, or a convex ultrasonic probe, or a sectored ultrasonic probe. In the case of performing scanning of a three-dimensional region (i.e., performing three-dimensional scanning) inside the subject P using the ultrasonic probe 1; for example, the user connects a mechanical 4D probe or a 2D array probe as the ultrasonic probe 1 to the device main body 10. A mechanical 4D probe is capable of performing two-dimensional scanning using a plurality of transducers arranged in an array in the same way as a 1D array probe, as well as is capable of performing three-dimensional scanning by making the plurality of transducers oscillate at a predetermined angle (an angle of oscillation). A 2D array probe is capable of performing three-dimensional scanning using a plurality of transducers arranged in a matrix, as well as is capable of performing two-dimensional scanning by collecting ultrasonic waves and transmitting them.

The display 2 is used to display a graphical user interface (GUI) for enabling the user of the ultrasonic diagnostic device 100 to input various instructions and various requests using the input interface 3, and to display ultrasonic images based on ultrasonic image data generated in the device main body 10. The display 2 represents an example of a display unit. The display 2 is implemented using a liquid crystal monitor or a CRT (Cathode Ray Tube) monitor.

The input interface 3 is implemented using a trackball, a switch, a dial, a foot switch, or a joystick. The input interface 3 receives input of various instructions and various requests from the user, and sends the instructions and the requests to the device main body 10.

The device main body 10 controls the transmission of ultrasonic waves by the ultrasonic probe 1, and controls the reception of reflected waves by the ultrasonic probe 1. That is, the device main body 10 controls the transmission and reception of ultrasonic waves by the ultrasonic probe 1. Then, based on the reflected-wave signals transmitted from the ultrasonic probe 1, the device main body 10 generates ultrasonic wave image data. The ultrasonic wave image data represents an example of image data. The device main body 10 is capable of generating two-dimensional ultrasonic wave image data based on the reflected-wave data that corresponds to a two-dimensional region inside the subject P and that is received by the ultrasonic probe 1. Moreover, the device main body 10 is capable of generating three-dimensional ultrasonic image data based on the reflected-wave data that corresponds to a three-dimensional region inside the subject P and that is received by the ultrasonic probe 1. As illustrated in FIG. 3, the device main body 10 includes a transceiver circuit 11, a buffer memory 12, B-mode processing circuitry 13, doppler processing circuitry 14, an image generating circuit 15, a memory 16, and processing circuitry 17.

The transceiver circuit 11 operates under the control of a control function 17*a* of the processing circuitry 17, and makes the ultrasonic probe 1 transmit ultrasonic waves and receive ultrasonic waves (i.e., the reflected waves of ultrasonic waves). That is, the transceiver circuit 11 performs ultrasonic scanning via the ultrasonic probe 1.

The transceiver circuit 11 operates under the control of the control function 17*a* of the processing circuitry 17, and makes the ultrasonic probe 1 transmit ultrasonic waves. The transceiver circuit 11 includes a rate pulse generating circuit, a transmission delay circuit, and a transmission pulser; and supplies drive signals to the ultrasonic probe 1. In the case of scanning a two-dimensional region inside the subject P, the transceiver circuit 11 makes the ultrasonic probe 1 transmit ultrasonic beams meant for scanning a two-dimensional region. In the case of scanning a three-dimensional region inside the subject P, the transceiver circuit 11 makes the ultrasonic probe 1 transmit ultrasonic beams meant for scanning a three-dimensional region.

The rate pulser generating circuit repeatedly generates rate pulses for the purpose of forming transmission ultrasonic waves (transmission beams) at a predetermined rate frequency (pulse repletion frequency: PRF). Since the rate pulses pass through the transmission delay circuit, a voltage gets applied to the transmission pulses in the state of having different transmission delay periods. For example, the transmission delay circuit applies, to each rate pulse generated by the rate pulse generating circuit, the transducer-by-transducer transmission delay time required in focusing the ultrasonic waves, which are generated from the ultrasonic probe 1, into a beam shape and deciding the transmission directionality. At the timings based on the rate pulses, the transmission pulses apply drive signals (drive pulses) to the transducers of the ultrasonic probe 1. Meanwhile, the transmission delay circuit varies the transmission delay period applied to each rate pulse, and arbitrarily adjusts the transmission direction of ultrasonic waves from the transducer surface.

The drive pulses reach the transducers in the ultrasonic probe 1 from the transmission pulses via a cable, and are then converted from being electrical signals into mechanical vibration in the transducers. The ultrasonic waves that are generated due to the mechanical vibration are transmitted to the inside of the tissues. Herein, the ultrasonic waves having a different transducer-by-transducer transmission delay period are focused and propagated in a predetermined direction.

Meanwhile, under the control of the control function 17*a* of the processing circuitry 17, the transceiver circuit 11 has the function of instantaneously varying the transmission frequency and the transmission drive voltage in order to execute a predetermined scanning sequence. Particularly, the variation in the transmission drive voltage is implemented by a linear-amplification-type transmission circuit capable of varying the value of the transmission drive voltage or a mechanism that electrically switches among a plurality of power source units.

The reflected waves of the ultrasonic waves, which were transmitted by the ultrasonic probe 1, reach the transducers inside the ultrasonic probe 1 and are then converted from mechanical vibration into electrical signals (reflected-wave signals) in the transducers. Then, the reflected-wave signals are input to the transceiver circuit 11. The transceiver circuit 11 further includes a preamplifier, an analog-to-digital converter (ADC), a reception delay circuit, an adder, and a quadrature detection circuit. Under the control of the control function 17*a* of the processing circuitry 17, the transceiver circuit 11 performs a variety of processing with respect to the reflected-wave signals based on the reflected waves received by the ultrasonic probe 1, and generates reflected-wave data. Then, the transceiver circuit 11 stores the reflected-wave data in the buffer memory 12.

The preamplifier amplifies the reflected-wave signal on a channel-by-channel basis, and performs gain adjustment (gain correction). The ADC performs A/D conversion and converts the reflected-wave signals, which have been subjected to gain correction, into digital signals. The reception delay circuit applies, to the digital signals, the reception delay period that is required in deciding the reception directionality. The adder performs an addition operation for adding the reflected-wave signals (digital signals) that have the reception delay period applied thereto by the reception delay circuit. As a result of the addition operation performed by the adder, the reflection component gets highlighted from the direction corresponding to the reception directionality of the reflected-wave signals. The signals obtained as a result of the addition operation are output as output signals from the adder. The quadrature detection circuit converts the output signals, which are output from the adder, into in-phase signals (I signals, I stands for In-phase) and quadrature signals (Q signals, Q stands for Quadrature) in the baseband bandwidth. Then, the quadrature detection circuit stores the I signals and the Q signals (i.e., IQ signals) as reflected-wave data in the buffer memory 12. Alternatively, the quadrature detection circuit can convert the output signals coming from the adder into radio frequency (RF) signals and store them in the buffer memory 12. The IQ signals or the RF signals represent the signals that include phase information (received signals). In the following explanation, the reflected-wave data output by the transceiver circuit 11 is sometimes referred to as received signals.

The transceiver circuit 11 generates two-dimensional reflected-wave data from the two-dimensional reflected-wave signals received by the ultrasonic probe 1. That is, the ultrasonic probe 1 and the transceiver circuit 11 perform ultrasonic wave scanning with respect to the subject P and collect the reflected-wave data. Herein, the ultrasonic probe 1 and the transceiver circuit 11 represent an example of a collecting unit.

The buffer memory 12 is used to temporarily store the reflected-wave data generated by the transceiver circuit 11.

For example, the buffer memory 12 is used to store the reflected-wave data equivalent to a few frames or the reflected-wave data equivalent to some volume. For example, under the control of the transceiver circuit 11, the reflected-wave data equivalent to a predetermined number of frames is stored in the buffer memory 12. Then, when the reflected-wave data equivalent to a predetermined number of frames is stored in the buffer memory 12, if the reflected-wave data equivalent to a single frame is newly generated by the transceiver circuit 11; then, under the control of the transceiver circuit 11, the reflected-wave data equivalent to the oldest frame is destroyed from the buffer memory 12 and the newly-generated reflected-wave data equivalent to a single frame is stored in the buffer memory 12. Regarding the reflected-wave data equivalent to a predetermined data volume, identical operations are performed in the buffer memory 12 under the control of the transceiver circuit 11. Meanwhile, the buffer memory 12 is implemented using, for example, a semiconductor memory device such as a random access memory (RAM) or a flash memory.

The B-mode processing circuitry 13 and the Doppler processing circuitry 14 are signal processing units that read the reflected-wave data from the buffer memory 12, and perform a variety of signal processing.

The B-mode processing circuitry 13 performs logarithmic amplification and envelop detection with respect to the reflected-wave data read from the buffer memory 12, and generates data (B-mode data) in which the signal intensity (the amplitude intensity) of each sample point is expressed as the level of luminance. Then, the B-mode processing circuitry 13 outputs the B-mode data to the image generating circuit 15. The B-mode processing circuitry 13 is implemented using, for example, a processor.

The Doppler processing circuitry 14 performs frequency analysis with respect to the reflected-wave data read from the buffer memory 12; extracts kinetic information of the movable bodies (the blood flow or the tissues, or the contrast dye echo component) based on the Doppler effect; and generates data (Doppler data) indicating the extracted kinetic information. For example, the Doppler processing circuitry 14 extracts, as the kinetic information of the mobile bodies, the mean velocity, the mean variance value, and the average power over a large number of points; and generates Doppler data indicating the extracted kinetic information of the mobile bodies. Then, the Doppler processing circuitry 14 outputs the Doppler data to the image generating circuit 15.

Using the functions of the Doppler processing circuitry 14, the ultrasonic diagnostic device 100 according to the first embodiment becomes able to implement a color Doppler method also called color flow mapping (CFM). In color flow mapping, the transmission and reception of ultrasonic waves is performed for a plurality of number of times over a plurality of scanning lines. In color flow mapping, the transmission and reception of ultrasonic waves is performed for a plurality of number of times in the same direction (over the same scanning lines), and blood flow signals are extracted from the signals that are received as the result. The data rows of the reflected-wave signals (reflected-wave data), which are obtained from the same position as a result of transmission and reception of ultrasonic waves, are called packets. The packet size represents the number of times for which ultrasonic waves are transmitted and received in the same direction in order to obtain blood flow information of a single frame. For example, the packet size is in the range of about five to 16. Subsequently, in color flow mapping, a moving target indicator (MTI) filter is applied with respect to the data rows at the same position; the signals originating from stationary tissues or from tissues having slow movement (i.e., clutter signals) are suppressed from the data rows at the same position; and the signals originating from the blood flow are extracted. Then, in color flow mapping, from the blood flow signals, blood flow information such as the mean velocity (velocity) of the blood flow, the mean variance value (variance) of the blood flow, and the average power value (power) of the blood flow is estimated. Subsequently, in color flow mapping, Doppler data is generated that indicates the estimated blood flow information. Then, the image generating circuit 15 (explained later) generates Doppler image data (color Doppler image data) that is, for example, two-dimensional color display of the distribution of the estimation result of the blood flow information indicated by the Doppler data. Then, under the control of the control function 17*a*, the display 2 displays a Doppler image based on the Doppler image data. The Doppler processing circuitry 14 is implemented using, for example, a processor.

The B-mode processing circuitry 13 and the Doppler processing circuitry 14 are capable of processing two-dimensional reflected-wave data as well as three-dimensional reflected-wave data.

The image generating circuit 15 generates ultrasonic wave image data from the data output by the B-mode processing circuitry 13 and the Doppler processing circuitry 14. From the two-dimensional B-mode data generated by the B-mode processing circuitry 13, the image generating circuit 15 generates two-dimensional B mode image data in which the intensity of the reflected waves is expressed in terms of luminosity. Moreover, from the two-dimensional Doppler data generated by the Doppler processing circuitry 14, the image generating circuit 15 generates two-dimensional Doppler image data in which the blood flow information is visualized. The two-dimensional Doppler image data represents velocity image data, variance image data, power image data, or image data obtained by combining those types of image data. From the Doppler data representing the blood flow information, the image generating circuit 15 generates, as Doppler image data, blood flow image data in which the blood flow information is displayed in color. The image generating circuit 15 is implemented using a processor.

Herein, generally, the image generating circuit 15 converts the scanning line signal sequence of ultrasonic wave scanning into a scanning line signal sequence of a video format represented by television (i.e., performs scanning conversion), and generates ultrasonic wave image data for display. For example, the image generating circuit 15 performs coordinate conversion according to the form of scanning of ultrasonic waves performed by the ultrasonic probe 1, and generates the ultrasonic image data for display. Moreover, the image generating circuit 15 performs a variety of image processing other than scanning conversion, such as performs image processing for regenerating images having average luminance using a plurality of image frames obtained after scanning conversion (i.e., performs smoothing), or performs image processing in which a differential filter is applied in the images (i.e., performs edge enhancement). Moreover, the image generating circuit 15 synthesizes character information of various parameters, calibration, and body marks with the ultrasonic wave image data.

Furthermore, the image generating circuit 15 performs coordinate conversion with respect to the three-dimensional B-mode data generated by the B-mode processing circuitry 13, and generates three-dimensional B-mode image data. Furthermore, the image generating circuit 15 performs coordinate conversion with respect to the three-dimensional Doppler data generated by the Doppler processing circuitry 14, and generates three-dimensional Doppler image data. That is, the image generating circuit 15 generates "three-dimensional B-mode image data and three-dimensional Doppler image data" as "three-dimensional ultrasonic wave image data (volume data)". Then, in order to generate a variety of two-dimensional image data meant for displaying the volume data in the display 2, the image generating circuit 15 performs various rendering operations with respect to the volume data.

For example, the rendering operations performed by the image generating circuit 15 include an operation of performing multi planar reconstruction (MPR) and generating MPR image data from the volume data. Moreover, for example, the rendering operations performed by the image generating circuit 15 include volume rendering (VR) for generating two-dimensional image data in which three-dimensional information is reflected.

The B-mode data and the Doppler data represent ultrasonic wave image data prior to scanning conversion; while the data generated by the image generating circuit 15 represents post-scanning-conversion ultrasonic wave image data for display. Meanwhile, the B-mode data and the Doppler data are also called raw data.

The memory 16 is used to store a variety of information and a variety of data. For example, the memory 16 is used to store a variety of image data generated by the image generating circuit 15. Moreover, the memory 16 is used to store the data generated by the B-mode processing circuitry 13 and the Doppler processing circuitry 14. The B-mode data and the Doppler data stored in the memory 16 is, for example, callable data that can be called by the operator after the diagnosis, and serves as the ultrasonic wave image data for display via the image generating circuit 15.

Moreover, the memory 16 is used to store a variety of data such as: control programs meant for implementing ultrasonic wave transmission-reception, image processing, and display processing; various other computer programs; diagnosis information (for example, the patient ID and the observations of the doctor); diagnosis protocols; and various body marks. The memory 16 is implemented using, for example, a semiconductor memory device such as a flash memory; or a hard disc; or an optical disc. Herein, the memory 16 represents an example of a memory unit.

The processing circuitry 17 controls the overall operations of the ultrasonic diagnostic device 100. As illustrated in FIG. 3, the processing circuitry 17 includes the control function 17a.

The control function 17a controls the processing (operations) of the transceiver circuit 11, the B-mode processing circuitry 13, the Doppler processing circuitry 14, and the image generating circuit 15 based on the instructions and the requests input by the operator via the input interface 3 and based on various control programs and a variety of data read from the memory 16. Moreover, the control function 17a controls the display 2 to display ultrasonic wave images based on a variety ultrasonic wave image data for display as stored in the memory 16.

Herein, for example, the control function 17a, which is a constituent element of the processing circuitry 17 illustrated in FIG. 3, is recorded as a computer-executable program in the memory 16. The processing circuitry 17 reads that computer program from the memory 16 and executes it to implement the control function 17a corresponding to the computer program. In other words, after the processing circuitry 17 reads the computer program, the control function 17a is included in the processing circuitry 17 as illustrated in FIG. 3. The processing circuitry 17 is implemented using, for example, a processor. Herein, the control function 17a represents an example of a control unit.

Till now, the explanation was given about an overall configuration of the ultrasonic diagnostic device 100 according to the first embodiment.

According to Patent Literature (Japanese Patent Application Laid-open No. 2011-125635) mentioned earlier, in the separation method for separating the clutter component and the blood flow component, quadrature transform is performed once with respect to the range (depth) direction and once with respect to the Doppler direction. However, regarding the depth direction, tissues and blood flow signals having different properties are included depending on the depth; and, if the reflected-wave data (received signals) including such tissues and blood flow signals is subjected to quadrature transform, signals having different properties get mixed.

In Patent Literature (Japanese Patent Application Laid-open No. 2011-125635), it is assumed that a normal linear MTI filter is applied in the Doppler direction, and since first-type quadrature transform and second-type quadrature transform are independent from each other, the abovementioned issue does not arise. However, as the second-type quadrature transform, when a nonlinear adaptive MTI filter that makes use of the statistical nature of the signals as disclosed in Patent Literature (Japanese Patent Application Laid-open No. 2014-158698) is applied, it is not desirable that the signals coming from the tissues having different properties are included in the reflected-wave data.

In that regard, in order to ensure that, by applying a nonlinear adaptive MTI filter with respect to the reflected-wave data (received signals) in which signals coming from the tissues having different properties are included, the artifact coming from an intensive reflector or a specular reflector can be reduced; the ultrasonic diagnostic device 100 according to the first embodiment is configured in the manner explained below.

Figure 4:
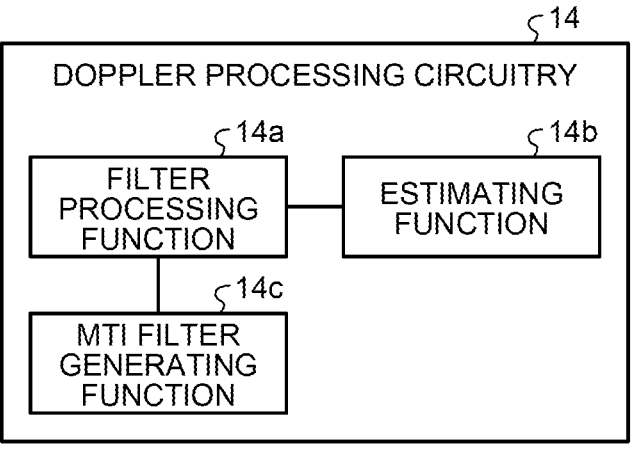
FIG. 4 is a diagram illustrating an exemplary configuration of Doppler processing circuitry according to the first embodiment.

FIG. 4 is a diagram illustrating an exemplary configuration of the Doppler processing circuitry 14 according to the first embodiment. As illustrated in FIG. 4, the Doppler processing circuitry 14 includes a filter processing function 14a, an estimating function 14b, and an MTI filter generating function 14c.

Herein, for example, the filter processing function 14a, the estimating function 14b, and the MTI filter generating function 14c, which are the constituent elements of the Doppler processing circuitry 14 illustrated in FIG. 4, are recorded as computer-executable programs in the memory 16. The Doppler processing circuitry 14 reads the computer programs from the memory 16, executes them, and implements the functions corresponding to them. In other words, after the Doppler processing circuitry 14 reads the computer programs, the functions illustrated in FIG. 4 are included in the Doppler processing circuitry 14.

Meanwhile, all processing functions, namely, the filter processing function 14a, the estimating function 14b, and the MTI filter generating function 14c can be collectively recorded as a single computer-executable program in the memory 16. In that case, the Doppler processing circuitry 14 reads that computer program from the memory 16, executes it, and implements the filter processing function 14a, the estimating function 14b, and the MTI filter generating function 14c corresponding to the computer program. The filter processing function 14a represents an example of a filter processing unit. The estimating function 14b represents an example of an estimating unit. The MTI filter generating function 14c represents an exemplary of a filter generating unit.

The filter processing function 14*a* performs short-time Fourier transform with respect to each of a plurality sets of partitioned data obtained by partitioning the reflected-wave data in the depth direction. Then, with respect to the received signal sequence that is in response to a plurality of times of ultrasonic transmission at each frequency and at each site, the filter processing function 14*a* applies a nonlinear adaptive MTI filter generated by the MTI filter generating function 14*c*. Subsequently, with respect to the data obtained as a result of application of the nonlinear adaptive MTI filter, the filter processing function 14*a* performs inverse short-time Fourier transform in the depth direction.

The estimating function 14*b* estimates, from the data subjected to inverse short-time Fourier transform, blood flow information such as the velocity, the power, and the variance of the blood flow.

The MTI filter generating function 14*c* generates a nonlinear adaptive MTI filter from the reflected-wave data.

Figure 5:
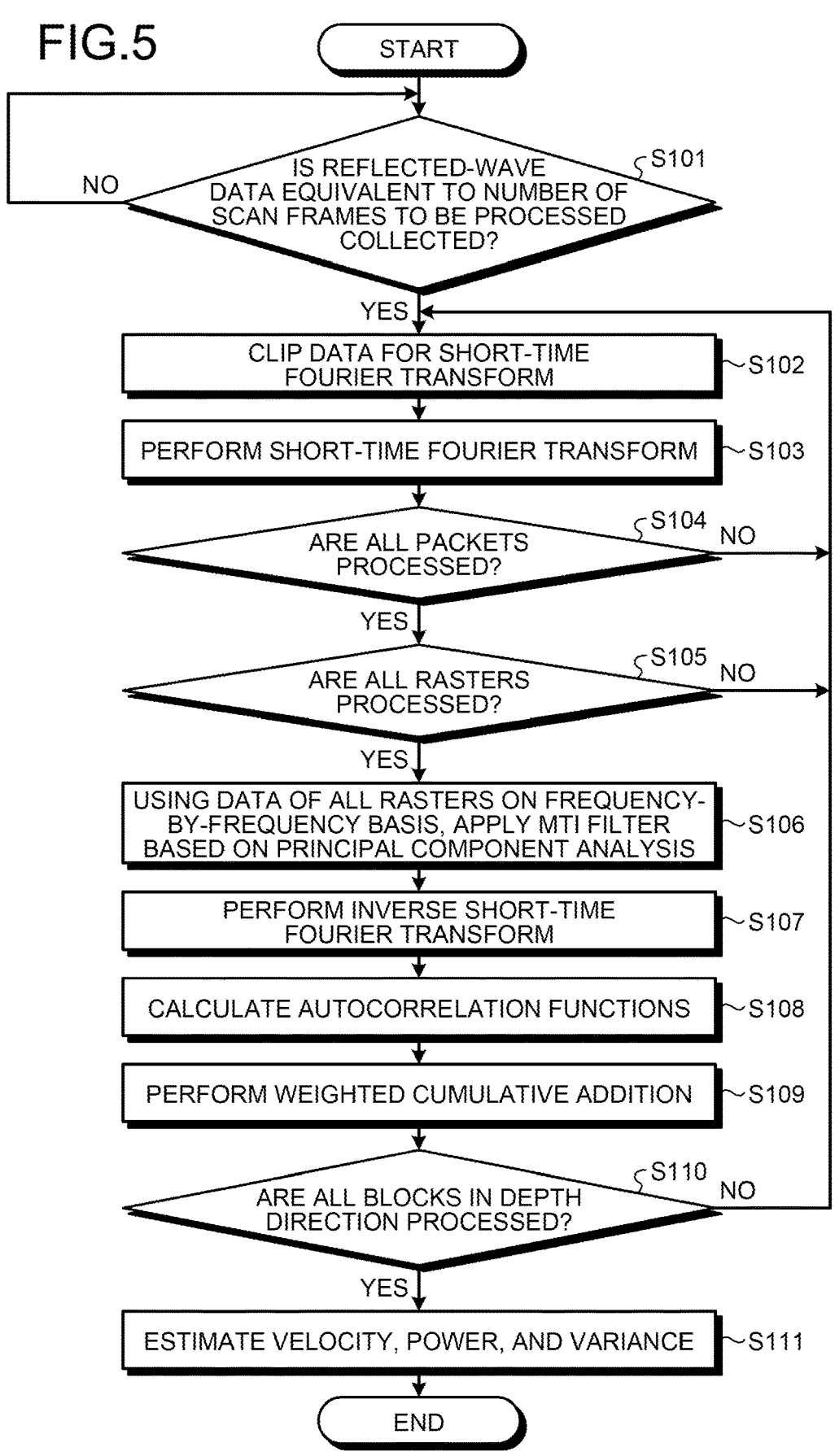
FIG. 5 is a flowchart for explaining an exemplary flow of operations performed by the Doppler processing circuitry according to the first embodiment.
Figure 6:
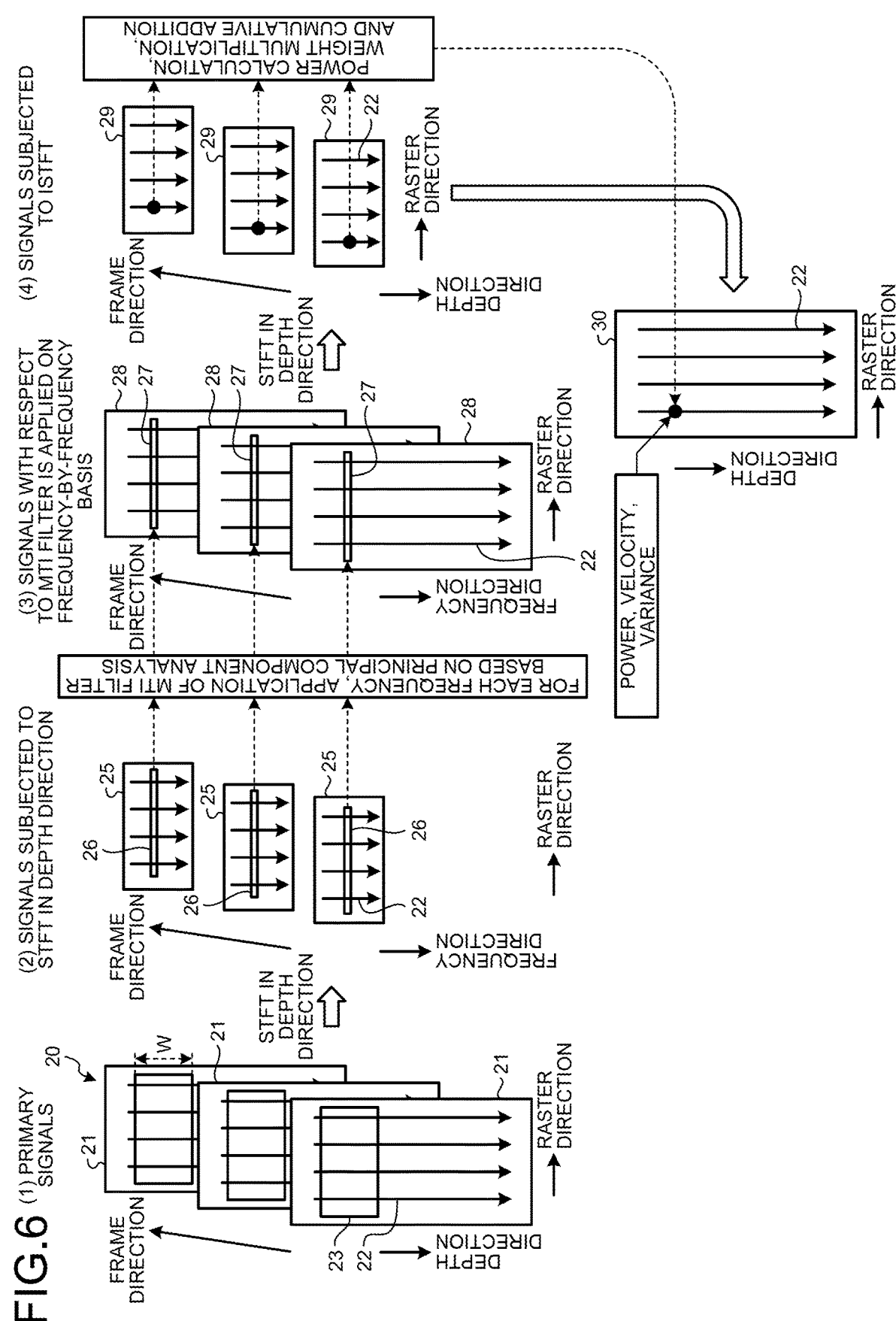
FIG. 6 is a diagram for explaining an example of the operations performed by the Doppler processing circuitry according to the first embodiment.

FIG. 5 is a flowchart for explaining an exemplary flow of operations performed by the Doppler processing circuitry 14 according to the first embodiment. FIG. 6 is a diagram for explaining an example of the operations performed by the Doppler processing circuitry 14 according to the first embodiment.

As illustrated in FIG. 5, the filter processing function 14*a* of the Doppler processing circuitry 14 determines whether or not the reflected-wave data equivalent to the number of scan frames to be processed (the data length to be processed) has been collected (Step S101). The following explanation is given about an exemplary data structure of the reflected-wave data to be processed. As illustrated in FIG. 6, reflected-wave data 20 to be processed is, for example, three-dimensional data formed by arranging a plurality of sets of two-dimensional reflected-wave data 21 in chronological order in the frame direction. For example, the three-dimensional reflected-wave data 20 contains the sets of two-dimensional reflected-wave data 21 equivalent to the number of scan frames to be processed. The ultrasonic probe 1 and the transceiver circuit 11 perform transmission and reception of ultrasonic waves of the entire range on a frame-by-frame basis, and collect a plurality of frames continuous in the frame direction (the reflected-wave data). As a result, the reflected-wave data 20 is obtained. The reflected-wave data 21 is two-dimensional data in which a plurality of sets of data of a plurality of sample points (at a plurality of positions), which is arranged on rasters (scanning lines) 22 along the depth direction, is arranged to be equal in number to the number of the rasters 22. In the example illustrated in FIG. 6, the reflected-wave data 21 contains a plurality of sets of data of a plurality of sample points on four rasters.

If the reflected-wave data equivalent to the number of scan frames to be processed is not yet collected (No at Step S101), then the filter processing function 14*a* again performs the operation at Step S101. On the other hand, if the reflected-wave data equivalent to the number of scan frames to be processed has been collected (Yes at Step S101), then the filter processing function 14*a* clips the target data for applying short-time Fourier transform (STFT) from the reflected-wave data 20 to be processed (Step S102). At Step S102, from among the sets of reflected-wave data 21 equivalent to the number of scan frames to be processed, with respect to a single set of reflected-wave data 21 that has not been subjected to the operation at Step S103 explained below, the filter processing function 14*a* sets a window 23 having a width "W" in the depth direction at the initial position in the depth direction. Then, the filter processing function 14*a* clips the target data (signals) for applying short-time Fourier transform on the data in the window 23. The clipped data (signals) is also called a "block". Meanwhile, for example, as illustrated in FIG. 6, the window 23 is set to include all rasters 22 in the reflected-wave data 21 (in the example illustrated in FIG. 6, four rasters).

Then, the filter processing function 14*a* applies short-time Fourier transform in the depth direction with respect to one of the blocks clipped at Step S102, and generates data (signals) 25 in which the depth direction of the block is converted into the frequency direction (the ultrasonic wave frequency direction) (Step S103). That is, at Step S103, the filter processing function 14*a* generates the data 25 in which the depth axis of the block is converted into the frequency axis. The data 25 contains data 26 corresponding to each frequency. That is, the data 25 contains a plurality of sets of data 26 corresponding to a plurality of frequencies.

Subsequently, the filter processing function 14*a* determines whether or not all packets (i.e., the data row in the frame direction at the same position) with respect to a raster have been applied short-time Fourier transform at Step S103 (Step S104).

If all the packets with respect to the raster are not yet applied short-time Fourier transform at Step S103 (No at Step S104), then the system control returns to Step S102. When the determination at Step S104 is negative (No at Step S104) and the system control returns to Step S102; with respect to the sets of reflected-wave data 21 that are not yet subjected to the operation at Step S103, the filter processing function 14*a* sets the windows 23 at the same positions of the windows 23 that were set in the previous instance of Step S102.

On the other hand, if all the packets with respect to the raster have been applied short-time Fourier transform at Step S103 (Yes at Step S104), then the system control proceeds to Step S105. At step S105, the filter processing function 14*a* determines whether or not the operation at Step S103 has been performed with respect to all the packets.

If the operation at Step S103 is not yet performed with respect to all the packets (No at Step S105), then the system control returns to Step S102. When the determination at Step S105 is negative (No at Step S105) and the system control returns to Step S102; the filter processing function 14*a* performs the identical operation to the operation performed when the determination at Step S104 is negative (No at Step S104) and the system control returns to Step S102. That is, in this instance of Step S102, with respect to the sets of reflected-wave data 21 that are not yet subjected to the operation at Step S103, the filter processing function 14*a* sets the windows 23 at the same positions of the windows 23 that were set in the previous instance of Step S102. Meanwhile, the term "packet" used in the explanation of Step S104 is usually used in color Doppler. However, with reference to FIG. 6, some portion a continuous frame is treated as a packet. Hence, in the explanation subsequent to the explanation with reference to FIG. 6, the term "packet" is sometimes substituted with the term "frame".

On the other hand, If the operation at Step S103 has been performed with respect to all the packets (Yes at Step S105), then the system control proceeds to Step S106.

At Step S106, as illustrated in FIG. 6, the filter processing function 14*a* applies a nonlinear adaptive MTI filter with respect to the data 26 corresponding to each of a plurality of frequencies, and extracts data (blood flow signals) 27 indicating the blood flow corresponding to the concerned frequency. Thus, by extracting a plurality of sets of data 27 corresponding to a plurality of frequencies, the filter processing function 14*a* extracts data (signals) 28 that contains the sets of data 27. More particularly, the filter processing function 14*a* extracts a single set of data 28 from a single set of data 25. Meanwhile, the nonlinear adaptive MTI filter used at Step S106 is generated by the MTI filter generating function 14*c*.

Then, the filter processing function 14*a* applies inverse short-time Fourier transform with respect to the data 28 and generates data (signals) 29 in which the frequency direction of the data 28 is converted into the depth direction (Step S107).

Figure 7:
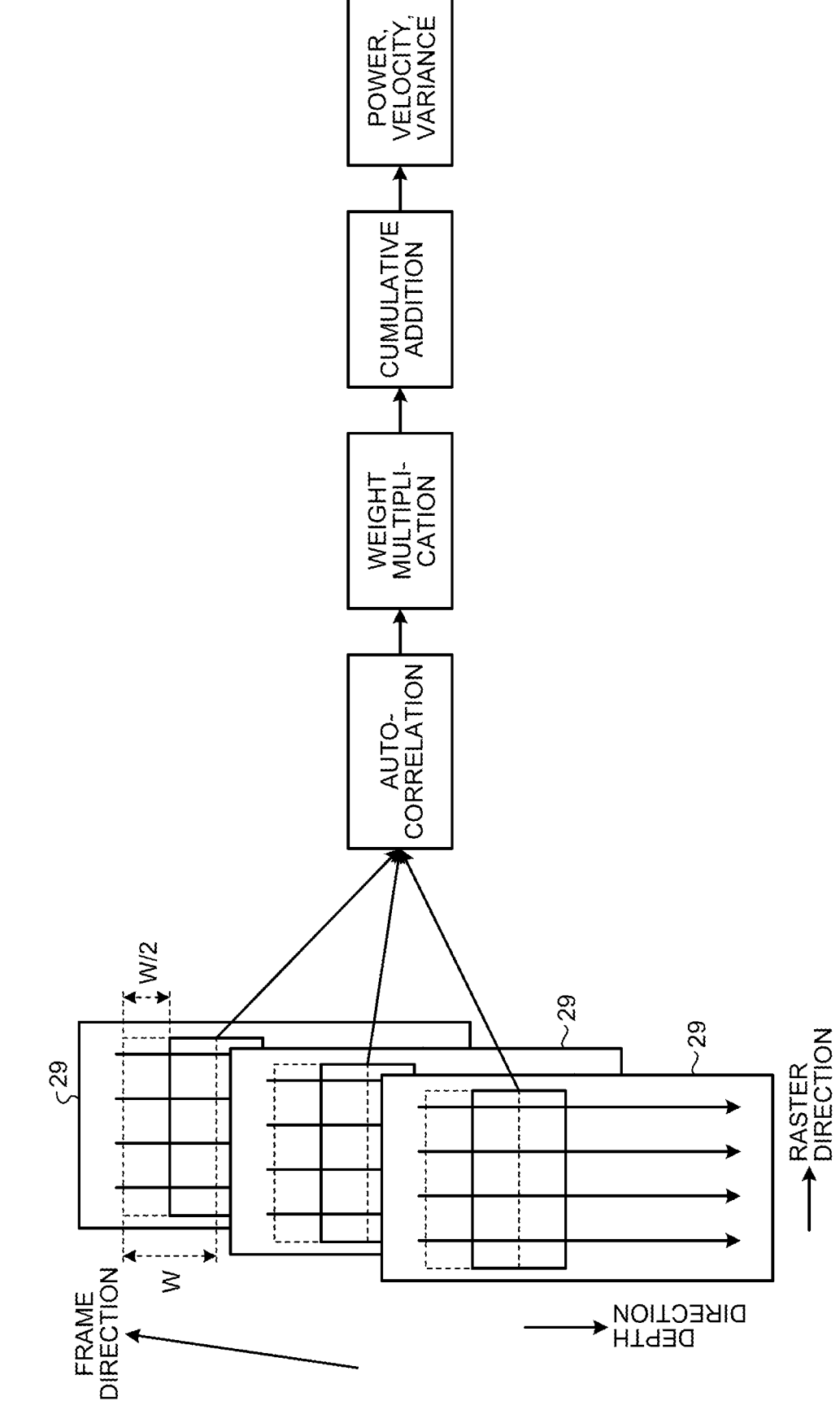
FIG. 7 is a diagram for explaining an example of the operations performed by an estimating function according to the first embodiment.

Then, from the data 29, the estimating function 14*b* calculates an autocorrelation function c0(t) of lag 0 and an autocorrelation function c1(t) of lag 1 (Step S108). For example, z(t, k) represents the data 29 obtained as a result of inverse short-time Fourier transform. Herein, "t" represents the time (position) in the depth direction, and "k" represents the time in the frame direction (the Doppler direction, or the packet direction). For example, FIG. 7 is a diagram for explaining an example of the operations performed by the estimating function 14*b* according to the first embodiment. As illustrated in FIG. 7, the estimating function 14*b* calculates the autocorrelation function c0(t) of the lag 0 according to Equation (1), and calculates the autocorrelation function c1(t) of the lag 1 according to Equation (2).

$$c0(t) = \sum_{k=1}^{L} z(t, k) z^*(t, k) \qquad (1)$$

$$c1(t) = \sum_{k=1}^{L-1} z(t+1, k) z^*(t, k) \qquad (2)$$

Figure 8:
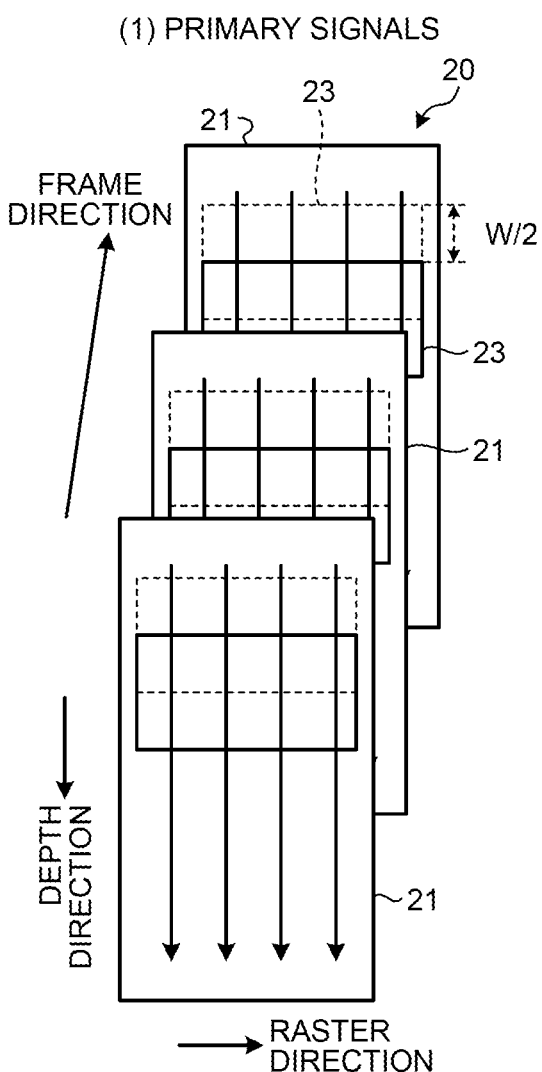
FIG. 8 is a diagram illustrating an exemplary setting method for setting windows according to the first embodiment.

Meanwhile, in the determination operation performed at Step S110 (explained later), if the determination is negative (No at Step S110); then, as illustrated in FIG. 8, the windows 23 are set with a shift of "W/2" therebetween in the depth direction. FIG. 8 is a diagram illustrating an exemplary setting method for setting the windows 23 according to the first embodiment. Thus, two blocks neighboring in the depth direction have an overlapping portion in the depth direction. More particularly, two blocks neighboring in the depth direction overlap by "W/2". For example, if the number of sets of data in the depth direction is equal to "1024", if the number of sets of data equivalent to the width "W" is "256", and if the number of sets of data equivalent to the shift amount "W/2" is "128"; then the reflected-wave data 21 is partitioned into seven blocks. Moreover, two blocks neighboring in the depth direction overlap by the shift amount "W/2".

Figure 9:
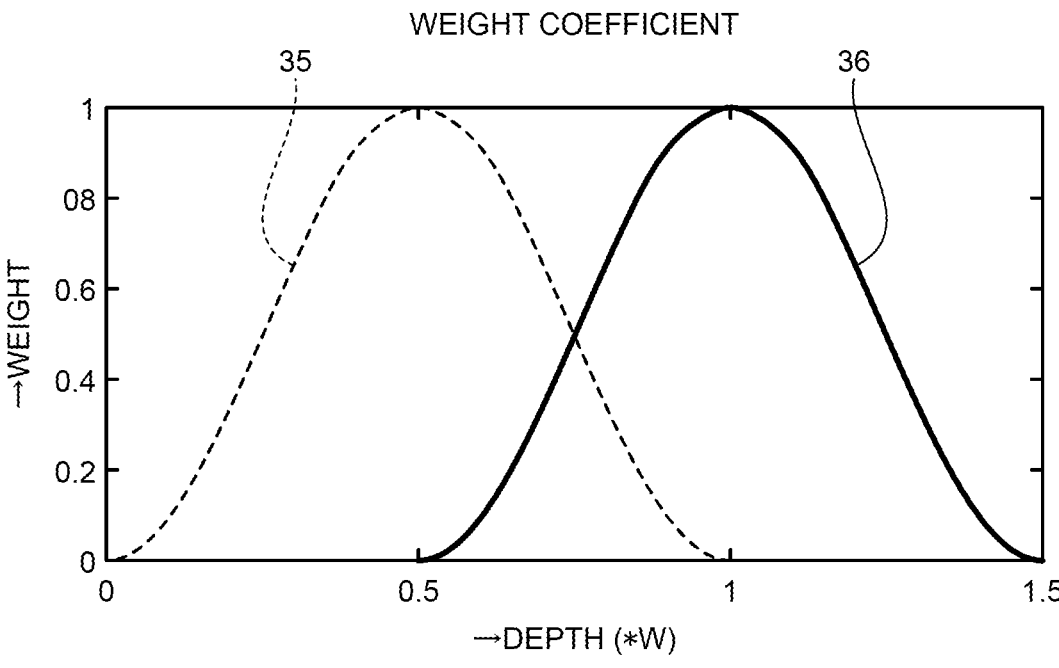
FIG. 9 is a diagram illustrating an example of a weight coefficient according to the first embodiment.

FIG. 9 is a diagram illustrating an example of a weight coefficient according to the first embodiment. In FIG. 9, the horizontal axis represents the position in the depth direction, and the vertical axis represents the weight. A position in the depth direction represented by the horizontal axis in FIG. 9 is illustrated by a value obtained by dividing the actual position in the depth direction by the width "W" (i.e., (the actual position in the depth direction)/W). Moreover, for example, in FIG. 7, the dashed-line frame in each set of data 29 corresponds to the window 23 set at the initial position, and the solid-line frame in each set of data 29 corresponds to the window 23 that is shifted from the initial position by the shift amount "W/2". The uppermost position of the dashed-line frame in each set of data 29 illustrated in FIG. 7 is equivalent to the depth "0". Moreover, regarding the overlapping portion between the dashed-line frame in each set of data 29 and the solid-line frame in that set of data 29, the range of the position in the depth direction is equal to or greater than "0.5" and equal to or smaller than "1.0". The lowermost position of the solid-line frame in each set of data 29 illustrated in FIG. 7 is equivalent to the depth "1.5".

A weight 35 illustrated in FIG. 9 is the weight applied to the autocorrelation functions c0(t) and c1(t) at each position in the hashed-line frame in each set of data 29 illustrated in FIG. 7; and represents a value corresponding to the position in the depth direction. Moreover, a weight 36 is the weight applied to the autocorrelation functions c0(t) and c1(t) at each position in the solid-line frame in each set of data 29 illustrated in FIG. 7; and represents a value corresponding to the position in the depth direction.

The estimating function 14*b* calculates the autocorrelation functions c0 and c1 at each position (Step S109). For example, the estimating function 14*b* calculates the product of the autocorrelation function c0(1) at each position in the hashed-line frame in each set of data 29 illustrated in FIG. 7 and the value of the weight 35 corresponding to the position in the depth direction. Moreover, the estimating function 14*b* calculates the product of the autocorrelation function c0(1) at each position in the solid-line frame in each set of data 29 illustrated in FIG. 7 and the value of the weight 36 corresponding to the position in the depth direction. Then, the estimating function 14*b* cumulatively adds the products at a position t and calculates an autocorrelation value "c0" at the position t.

Moreover, for example, the estimating function 14*b* calculates the product of the autocorrelation function c1(t) at each position in the hashed-line frame in each set of data 29 illustrated in FIG. 7 and the value of the weight 35 corresponding to the position in the depth direction. Moreover, the estimating function 14*b* calculates the product of the autocorrelation function c1(1) at each position in the solid-line frame in each set of data 29 illustrated in FIG. 7 and the value of the weight 36 corresponding to the position in the depth direction. Then, the estimating function 14*b* cumulatively adds the products at the position t and calculates an autocorrelation value "c1" at the position t.

Subsequently, the estimating function 14*b* determines whether or not the windows 23 are set at all positions in the depth direction of the reflected-wave data 21 and whether or not operations have been performed with respect to the blocks at all positions in the depth direction of the reflected-wave data 21 (Step S110). If the operations are not yet performed with respect to the blocks at all positions in the depth direction of the reflected-wave data 21 (No at Step S110), then the system control returns to Step S102. At Step S102, as illustrated in FIG. 8, the filter processing function 14*a* sets the windows 23 by shifting them from the current position in the depth direction by the shift amount "W/2" in the depth direction, and clips the data in the windows 23. Then, the filter processing function 14*a* and the estimating function 14*b* use the clipped data and perform the operations from Step S103 onward. More particularly, the filter processing function 14*a* and the estimating function 14*b* use the clipped data and perform identical operations to the operations performed from Step S103 onward when the windows 23 are set at the initial position.

On the other hand, if the operations have been performed with respect to the blocks at all positions in the depth direction of the reflected-wave data 21 (No at Step S110), then the estimating function 14*b* estimates a power Po, a velocity Ve, and a variance Var of the blood flow at each position (Step S111).

For example, as illustrated in FIG. 7, the estimating function 14*b* uses the autocorrelation functions c0 and c1 at each position and, according to Equation (3), calculates and estimates the power Po, the velocity Ve, and the variance Var of the blood flow at each position.

$$Po = c0 \tag{3}$$

$$Ve = \text{atan2}(imag(c1), real(c1))$$

$$Var = 1 - \frac{|c1|}{c0}$$

In Equation (3), "a tan 2" represents an arc tangent function for outputting an angle in the range of "$-\pi$ to $+\pi$". Moreover, "imag(c1)" represents a function for outputting only the imaginary part from the autocorrelation function c1 that is a complex number. Furthermore, "real(c1)" represents a function for outputting only the real part from the autocorrelation function c1.

Then, as illustrated in FIG. 6, the estimating function 14*b* generates Doppler data 30 that indicates the blood flow information containing the power Po, the velocity Ve, and the variance Var of the blood flow at each position. Subsequently, as explained earlier, the image generating circuit 15 generates Doppler image data (color Doppler image data) in which the distribution of the estimation result of the blood information indicated by the Doppler data 30 is, for example, displayed in color in a two-dimensional manner. Then, the control function 17*a* displays, in the display 2, a Doppler image based on the Doppler image data.

Figure 10:
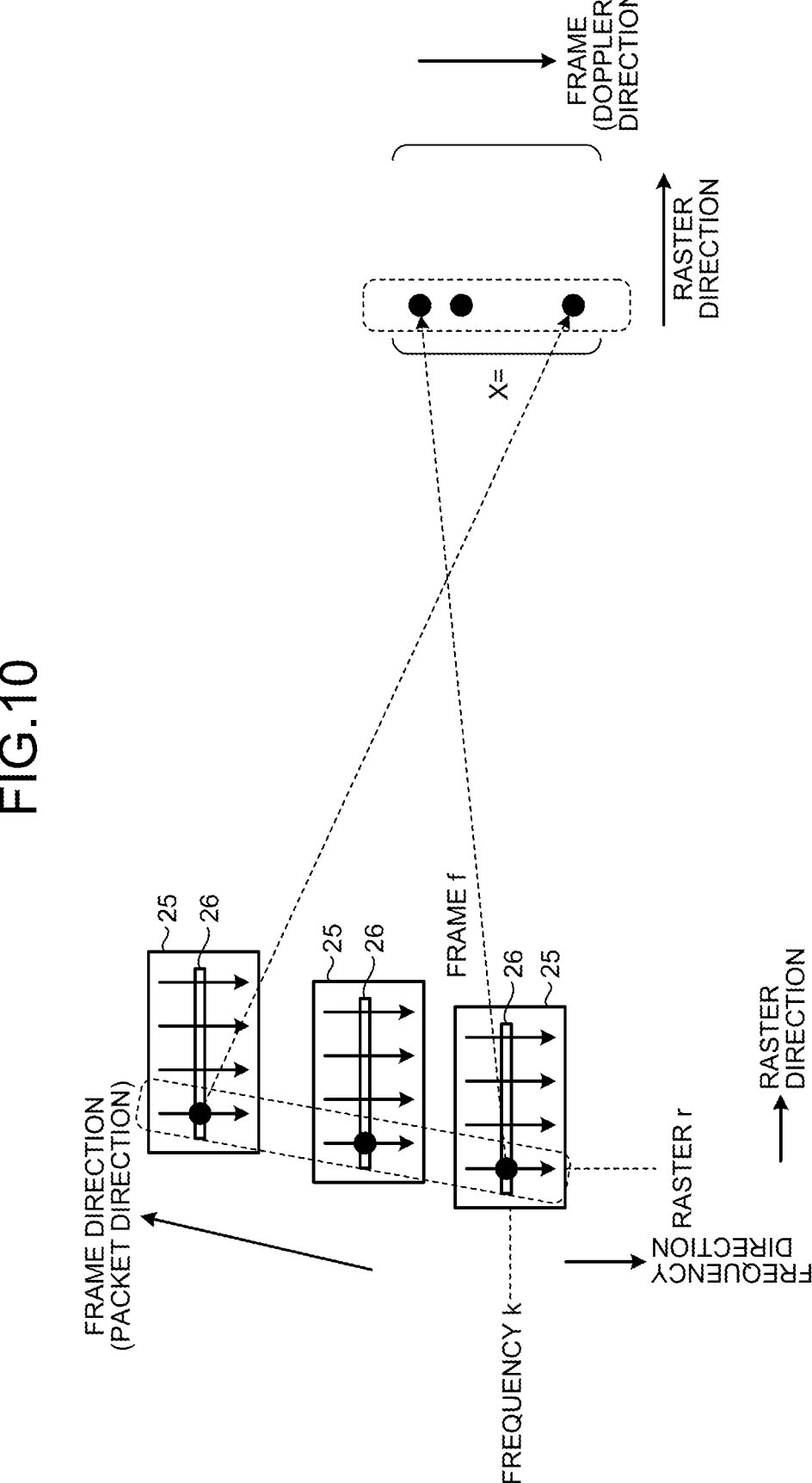
FIG. 10 is a diagram for explaining an example of the operations performed by an MTI filter generating function according to the first embodiment.

Given below is the explanation of an example of the operations performed by the MTI filter generating function 14*c* for generating a nonlinear adaptive MTI filter used at Step S106. FIG. 10 is a diagram for explaining an example of the operations performed by the MTI filter generating function 14*c* according to the first embodiment.

In the first embodiment, as illustrated in FIG. 10, the MTI filter generating function 14*c* uses the data 25 generated by the filter processing function 14*a*, and generates a nonlinear adaptive MTI filter. The data 25 is obtained when short-time Fourier transform is performed with respect to a single block in the depth direction, and the depth direction of the block is converted into the frequency direction (the ultrasonic wave frequency direction).

The MTI filter generating function 14*c* generates an MTI filter for each frequency. More particularly, the MTI filter generating function 14*c* uses a plurality of sets of data 26 that corresponds to a plurality of frequencies and that is included in the data 25, generates an MTI filter for each frequency.

For example, given below is the explanation of the case in which the MTI filter generating function 14*c* generates an MTI filter corresponding to a frequency k illustrated in FIG. 10, from among a plurality of frequencies. For example, when the data 26 corresponding to the frequency k illustrated in FIG. 10 is the only target data for processing, it becomes two-dimensional data in the raster direction and the frame direction (the packet direction, or the Doppler direction). The MTI filter generating function 14*c* defines that two-dimensional data as a matrix X having rows in the frame direction and having columns in the raster direction.

Then, the MTI filter generating function 14*c* generates a correlation matrix Rxx using Equation (4) given below.

$$R_{xx} = XX^H \tag{4}$$

In Equation (4), "$X^H$" represents the complex conjugate transpose matrix of the matrix X.

The eigenvalue decomposition of the correlation matrix Rxx is given below in Equation (5).

$$R_{xx} = VDV^H \tag{5}$$

In Equation (5), "V" represents an eigenvector matrix; "D" represents a diagonal matrix in which the diagonal elements are eigenvalues; and "$V^H$" represents the complex conjugate transpose matrix of the eigenvector matrix V. The eigenvector matrix V is a matrix in which a plurality of eigenvectors is arranged in descending order of the corresponding eigenvalues. The diagonal matrix D is a matrix in which the eigenvalues are arranged in a descending order. Herein, approximation of signals with only a predetermined number of eigenvectors having large eigenvalues is called principal component analysis. In the first embodiment, the MTI filter generating function 14*c* treats the signals (clutter signals) from the tissues as the principal component, and generates a nonlinear adaptive MTI filter in which signals (data) obtained by subtracting the principal component signals from the primary signals (the data 26) are treated as the blood flow signals. The MTI filter generating function 14*c* generates an MTI filter matrix W according to Equation (6) given below.

$$W = V \begin{pmatrix} 0 & & & & \\ & 0 & & & \\ & & \ddots & & \\ & & & 1 & \\ & & & & 1 \end{pmatrix} V^H \tag{6}$$

In the right-hand side in Equation (6), the matrix in between the eigenvector matrix V and the complex conjugate transpose matrix $V^H$ of the eigenvector matrix V is a diagonal matrix. The number of principal components to be reduced, that is, the number of ranks to be reduced is determined depending on the number of diagonal elements equal to "0" in the diagonal matrix. Hereinafter, the number of ranks to be reduced is written as a "rank cut count". The rank cut count can be a predetermined value. Alternatively, the MTI filter generating function 14*c* can adaptively decide on the rank cut count based on the magnitude of the eigenvalues, as explained in Patent Literature (Japanese Patent Application Laid-open No. 2014-158698) mentioned earlier.

Subsequently, according to Equation (7) given below, the filter processing function 14*a* calculates a signal matrix Y after the passage through the MTI filter.

$$Y = WX \tag{7}$$

The signal matrix Y given in Equation (7) represents the data 27 corresponding to the frequency k as illustrated in FIG. 6.

Meanwhile, the MTI filter generating function 14*c* can calculate the eigenvector matrix V according to singular value decomposition given below in Equation (8).

$$X^H = USV^H \tag{8}$$

In Equation (8), "S" represents a diagonal matrix in which the diagonal elements are singular values. The squares of the singular values are equal to the eigenvalues of the correlation matrix Rxx.

Meanwhile, in the various operations explained above, the Doppler processing circuitry 14 can partition a plurality of sets of data in the frame direction into groups of a predetermined number of sets of data that are continuous in the frame direction, and can perform the operations with respect to each group of a predetermined number of sets of data. In that case, the Doppler processing circuitry 14 can perform the partitioning in such a way that there is some overlapping data. As a result of having some overlapping data, for example, the result of previously-calculated short-time Fourier transform of the concerned frame can be used, thereby enabling achieving enhancement in the processing velocity.

Till now, the explanation was given about the ultrasonic diagnostic device 100 according to the first embodiment. According to the first embodiment, since the MTI filter matrix W is calculated within the partitioned range, the movement can be understood in a local manner. Moreover, since a nonlinear adaptive MTI filter is applied on a frequency-by-frequency basis, it becomes possible to hold down the fluctuation in the amplitude attributed to the amplitude modulation that is dependent on the azimuth resolution. Hence, according to the first embodiment, it becomes possible to reduce the lingering clutter attributed to the intensive reflection of an intensive reflector or the specular reflection of a specular reflector such as a thoracic diaphragm.

As explained above, the ultrasonic probe 1 and the transceiver circuit 11 perform ultrasonic scanning with respect to the subject P and collect reflected-wave data. The filter processing function 14a performs short-time Fourier transform in the depth direction with respect to the reflected-wave data 20; applies a nonlinear adaptive MTI filter on a frequency-by-frequency basis with respect to the result of short-time Fourier transform; and performs inverse short-time Fourier transform in the depth direction with respect to the output of the nonlinear adaptive MTI filter. The estimating function 14b estimates the blood flow information from the result of inverse short-time Fourier transform. Thus, according to the first embodiment, with respect to the reflected-wave data (the received signals) containing signals from tissues having different properties, the artifact from an intensive reflector or a specular reflector can be reduced using a nonlinear adaptive MTI filter.

Moreover, in the first embodiment, the filter processing function 14a partitions the reflected-wave data 20 into a plurality of sets of data having partial overlapping in the depth direction and, with respect to each set of partitioned data, performs short-time Fourier transform in the depth direction. Then, the filter processing function 14a applies a nonlinear adaptive MTI filter on a frequency-by-frequency basis with respect to the result of short-time Fourier transform, and performs inverse short-time Fourier transform with respect to the output of the nonlinear adaptive MTI filter. The estimating function 14b estimates the blood flow information based on the weight-added autocorrelation functions at the same position.

Moreover, as explained above, in the first embodiment, the nonlinear adaptive MTI filter reduces the clutter component according to the method of principal component analysis.

Furthermore, at the time of performing short-time Fourier transform and inverse short-time Fourier transform, the filter processing function 14a usually uses a window function such as Hamming. However, at the time of performing short-time Fourier transform and inverse short-time Fourier transform, the filter processing function 14a need not use a window function. The reason for that is explained below. The MTI filter applied in the frame direction is a bypass filter. Hence, at the time of performing short-time Fourier transform, even if a window function is not used thereby resulting in the generation of harmonic waves due to discontinuous edges, the MTI filter can remove the harmonic waves as long as they are uniform in the frame direction. In the inverse short-time Fourier transform, the blood flow signals after the passage through the MTI filter are close to irregular signals. Hence, even if discontinuity at the edges is not taken into account, it is not much of an issue. Thus, the filter processing function 14a can decide on whether or not to use a window function depending on the situation. Moreover, the filter processing function 14a can decide on whether or not to use a window function based on a user instruction. For example, such an instruction indicates whether or not to use a window function, and is input by the user via the input interface 3.

Meanwhile, in the first embodiment, the explanation is given for the case in which two windows 23 neighboring in the depth direction overlap and two blocks neighboring in the depth direction overlap. However, neither two windows 23 neighboring in the depth direction nor two blocks neighboring in the depth direction need to overlap.

Moreover, in the first embodiment, the explanation is given for the case in which the filter processing function 14a partitions the reflected-wave data 21 into a plurality of blocks. However, the filter processing function 14a can perform the operations without partitioning the reflected-wave data 21 by setting the partition count to "1". The following is one of a plurality of differences between the first embodiment and Patent Literature (Japanese Patent Application Laid-open No. 2011-125635) mentioned earlier. For example, in Patent Literature (Japanese Patent Application Laid-open No. 2011-125635), it is assumed that a linear MTI filter is applied in the Doppler direction. In contrast, in the first embodiment, a nonlinear adaptive MTI filter is applied.

Moreover, in the first embodiment, the Doppler direction is used synonymously with the frame direction assuming that the scanning disclosed in Patent Literature (Japanese Patent Application Laid-open No. 2014-158698) is performed. In commonly-used color Doppler scanning, either the same raster is transmitted for a plurality of number of times and then the next raster is transmitted for a plurality of number of times; or a plurality of rasters is treated as a block that is repeatedly transmitted, and then the next block is transmitted. In this case, the data rows at the same site are called packets. The direction of the packet rows represents the Doppler direction. In the first embodiment is explained a peculiar example corresponding to the case in which a single block represents all rasters. Even in the normal scanning in which the Doppler direction does not represent the frame direction but represents the packet direction, the first embodiment can be implemented.

Furthermore, in the first embodiment, the estimating function 14b performs weighted addition of the autocorrelation functions $c_0(t)$ and $c_1(t)$ at the same position and calculates the blood flow information based on the weight-added autocorrelation functions. However, alternatively, the estimating function 14b can perform weighted addition of the sets of data 29; calculate the autocorrelation functions $c_0(t)$ and $c_1(t)$ from the weight-added sets of data 29; and estimate the blood flow information based on the calculated autocorrelation functions.

Second Embodiment

In the first embodiment, the explanation is given about the case in which the ultrasonic diagnostic device 100 performs various operations. Alternatively, an image processing device can perform various operations identical to the operations performed by the ultrasonic diagnostic device 100. That explanation is given below as a second embodiment.

Figure 11:
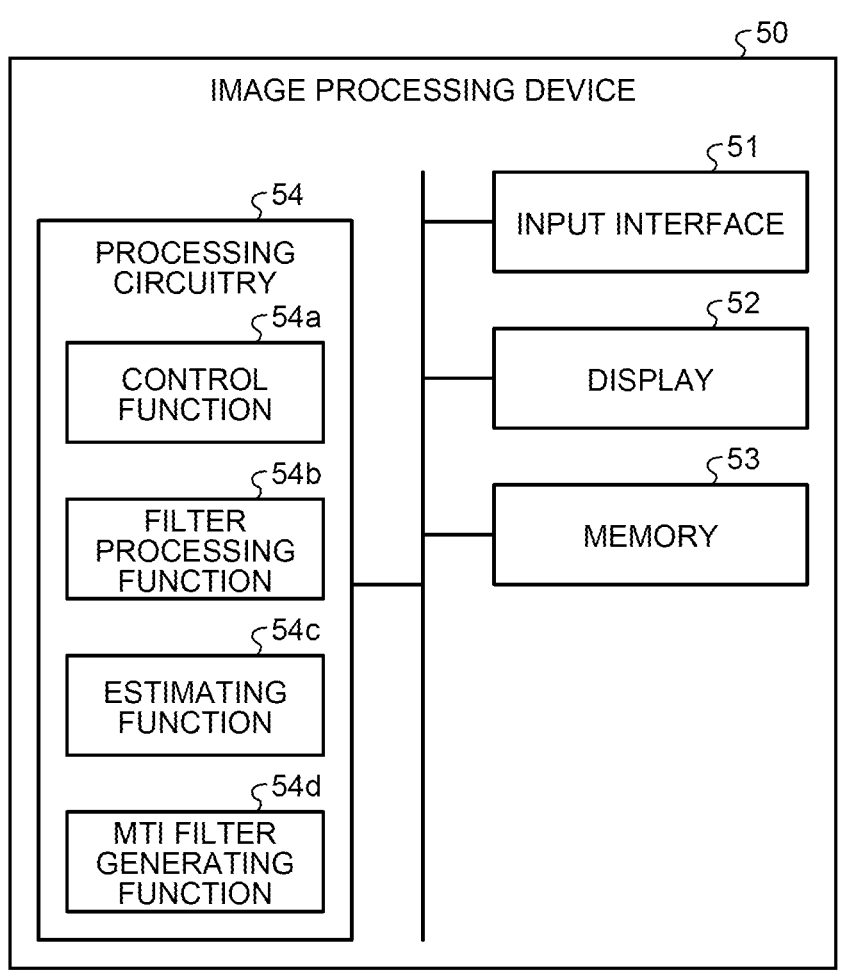
FIG. 11 is a diagram illustrating an exemplary configuration of an image processing device according to a second embodiment.

FIG. 11 is a diagram illustrating an exemplary configuration of an image processing device 50 according to the second embodiment. The image processing device 50 obtains the three-dimensional reflected-wave data 20 from the ultrasonic diagnostic device 100 via a network, and performs identical operations to the operations performed by the ultrasonic diagnostic device 100 with respect to the reflected-wave data 20. For example, the image processing device 50 generates the Doppler data 30 indicating the blood flow information from the reflected-wave data 20. Then, the image processing device 50 generates color Doppler image data in which the distribution of the estimation result of the blood flow information indicated by the Doppler data is, for example, displayed in color in a two-dimensional manner. Subsequently, the image processing device 50 displays a color Doppler image, which is based on the color Doppler data, in a display 52.

FIG. 11 is a diagram illustrating an exemplary configuration of the image processing device 50 according to the second embodiment. As illustrated in FIG. 11, the image processing device 50 includes an input interface 51, the display 52, a memory 53, and processing circuitry 54.

The input interface 51 is connected to the processing circuitry 54 and outputs thereto electrical signals obtained by converting the input operations received from the operator. Meanwhile, the input interface 51 mentioned in the present written description is not limited to include a physical operation component such as a mouse or a keyboard. Alternatively, for example, examples of the input interface include processing circuitry that receives electrical signals corresponding to an input operation from an external input device installed separately, and outputs the electrical signals to a control circuit.

For example, the input interface 51 is implemented using: a trackball meant for performing a variety of setting; or switch buttons; or a mouse; or a keyboard; or a touch-sensitive pad that has an operation surface for touching and performing input operations; or a touch-sensitive screen having a display surface and a touch-sensitive pad configured in an integrated manner; or a contactless input interface in which an optical sensor is used; or a voice input interface.

The display 52 is connected to the processing circuitry 54 and is used to display a variety of information and various images output from the processing circuitry 54. For example, the display 52 is implemented using a liquid crystal monitor, a cathode ray tube (CRT) monitor, or a touch-sensitive panel. For example, the display 52 is used to display a graphical user interface (GUI) meant for receiving instructions from the operator; receiving various images for display; and receiving various processing results obtained by the processing circuitry. The display 52 represents an example of a display unit.

The memory 53 is connected to the processing circuitry 54 and is used to store a variety of data. For example, the memory 53 is implemented using a semiconductor memory device such as a random access memory (RAM) or a flash memory; or a hard disc; or an optical disc. In the second embodiment, the memory 53 is used to store the three-dimensional reflected-wave data 20. Herein, the memory 53 represents an example of a memory unit.

Moreover, the memory 53 is used to store a variety of information used in the processing by the processing circuitry 54; and to store the processing results obtained by the processing circuitry 54. For example, the memory 53 is used to store image data for display as generated by the processing circuitry 54.

The processing circuitry 54 is implemented using a processor. The processing circuitry 54 includes a control function 54a, a filter processing function 54b, an estimating function 54c, and an MTI filter generating function 54d.

The control function 54a controls the entire image processing device 50. For example, the control function 54a displays various images, which are based on a variety of image data stored in the memory 53, in the display 52.

The filter processing functions 54b, the estimating function 54c, and the MTI filter generating function 54d perform operations with respect to the reflected-wave data 20 stored in the memory 53 in an identical manner to the operations performed by the filter processing function 14a, the estimating function 14b, and the MTI filter generating function 14c, respectively. For example, the filter processing function 54b performs identical operations to the operations performed by the filter processing function 14a. The estimating function 54c performs identical operations to the operations performed by the estimating function 14b. The MTI filter generating function 54d performs identical operations to the operations performed by the MTI filter generating function 14c. The filter processing function 54b represents an example of a filter processing unit. The estimating function 54c represents an example of an estimating unit. The MTI filter generating function 54d represents an example of a filter generating unit.

Till now, the explanation was given about the image processing device 50 according to the second embodiment. According to the second embodiment, it becomes possible to achieve identical effects to the effects achieved in the first embodiment.

In the explanation given above, the term "processor" implies, for example, a central processing unit (CPU), a graphics processing unit (GPU), an application specific integrated circuit (ASIC), or a programmable logic device (for example, a simple programmable logic device (SPLD), or a complex programmable logic device (CPLD), or a field programmable gate array (FPGA)). The processor reads computer programs stored in the memory 16 or the memory 53, and executes them to implement the functions. Meanwhile, instead of storing the computer programs in the memory 16 or the memory 53, they can be directly embedded in the circuit of the processor. In that case, the processor reads the computer programs embedded in its circuit, and executes them to implement the functions. Meanwhile, the processor according to the embodiments are not limited to be configured to have a single circuit for the entire processor. Alternatively, a single processor can be configured using a combination of a plurality of independent circuits for implementing the functions of the processor.

According to at least one of the embodiments described above, in the ultrasonic diagnostic device 100 or the image processing device 50, with respect to the reflected-wave data (the received signals) that contain signals from tissues having different properties, a nonlinear adaptive MTI filter is applied so that the artifact from intensive reflectors or specular reflectors can be reduced.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirits of the inventions.

What is claimed is:

1. An ultrasonic diagnostic device, comprising:

a collector that performs ultrasonic scanning with respect to a subject and collects reflected-wave data; and processing circuitry configured to perform a short-time Fourier transform in a depth direction with respect to a plurality of sets of partitioned data acquired by partitioning the reflected-wave data in the depth direction, apply a nonlinear adaptive MTI filter on a frequency-by-frequency basis with respect to a result of the performance of the short-time Fourier transform, wherein the nonlinear adaptive MTI filter is a filter to reduce principal component signals by performing principal component analysis to two-dimensional data, in a raster direction and a frame direction, with a same frequency in the result of the short-time Fourier transform, the MTI filter being generated on a frequency-by-frequency basis by using the two-dimensional data corresponding to each frequency, in the raster direction and the frame direction, for each corresponding frequency, perform an inverse short-time Fourier transform in the depth direction with respect to an output of the nonlinear adaptive MTI filter to generate a plurality of pieces of data transformed in the depth direction, and estimate blood flow information from the data generated by performing the inverse short-time Fourier transform.

2. The ultrasonic diagnostic device according to claim 1, wherein the processing circuitry is further configured to:

partition the reflected-wave data in the depth direction into a plurality of blocks as the plurality of sets of the partitioned data so that two blocks neighboring in the depth direction overlap, and estimate the blood flow information based on weight-added autocorrelation functions at a same position.

3. The ultrasonic diagnostic device according to claim 1, wherein the nonlinear adaptive MTI filter is a filter for reducing clutter component according to a method based on the principal component analysis.

4. The ultrasonic diagnostic device according to claim 1, wherein the collector performs transmission and reception of ultrasonic waves of an entire range on a frame-by-frame basis, and collects a plurality of frames continuous in a frame direction.

5. An image processing device, comprising:

a memory storing reflected-wave data collected as a result of performing ultrasonic scanning with respect to a subject; and processing circuitry configured to:

perform a short-time Fourier transform in a depth direction with respect to a plurality of sets of partitioned data acquired by partitioning the reflected-wave data in the depth direction, apply a nonlinear adaptive MTI filter on a frequency-by-frequency basis with respect to a result of the performance of the short-time Fourier transform, wherein the nonlinear adaptive MTI filter is a filter to reduce principal component signals by performing principal component analysis to two-dimensional data, in a raster direction and a frame direction, with a same frequency in the result of the short-time Fourier transform, the MTI filter being generated on a frequency-by-frequency basis by using the two-dimensional data corresponding to each frequency, in the raster direction and the frame direction, for each corresponding frequency, perform inverse short-time Fourier transform in the depth direction with respect to an output of the nonlinear adaptive MTI filter to generate a plurality of pieces of data transformed in the depth direction, and estimate blood flow information from the data generated by performing the inverse short-time Fourier transform.

6. The ultrasonic diagnostic device according to claim 1, wherein the processing circuitry is further configured to add the plurality of the pieces of the data generated by performing the inverse short-time Fourier transform while over-wrapping overlapping the plurality of the pieces of the data.

7. The ultrasonic diagnostic device according to claim 1, wherein two blocks neighboring in the depth direction overlap by half of a number of sets of data corresponding to each of the plurality of the blocks.

* * * * *